(12) United States Patent
Kadomatsu et al.

(10) Patent No.: US 8,754,036 B2
(45) Date of Patent: Jun. 17, 2014

(54) METHOD FOR TREATING NEUROPATHIC PAIN

(71) Applicants: National University Corporation Nagoya University, Nagoya (JP); Seikagaku Corporation, Tokyo (JP)

(72) Inventors: Kenji Kadomatsu, Aichi (JP); Yukihiro Matsuyama, Aichi (JP); Akiomi Tanaka, Tokyo (JP); Sawako Takeshita, Tokyo (JP)

(73) Assignees: National University Corporation Nagoya University, Nagoya-shi (JP); Seikagaku Corporation, Tokyo (JP)

( * ) Notice: Subject to any disclaimer, the term of this patent is extended or adjusted under 35 U.S.C. 154(b) by 0 days.

(21) Appl. No.: 13/778,359

(22) Filed: Feb. 27, 2013

(65) Prior Publication Data

US 2013/0164276 A1 Jun. 27, 2013

Related U.S. Application Data

(62) Division of application No. 12/667,178, filed as application No. PCT/JP2008/061834 on Jun. 30, 2008, now abandoned.

(30) Foreign Application Priority Data

Jun. 29, 2007 (JP) ................................. 2007-173487

(51) Int. Cl.
| | | |
|---|---|---|
| *A61K 38/00* | (2006.01) | |
| *A61K 38/02* | (2006.01) | |
| *A61K 38/43* | (2006.01) | |
| *A61K 38/46* | (2006.01) | |
| *A61K 38/48* | (2006.01) | |
| *A61P 25/02* | (2006.01) | |

(52) U.S. Cl.
USPC ............. 514/1.1; 514/1.2; 514/1.3; 514/17.7; 514/17.8; 514/18.2; 514/18.3

(58) Field of Classification Search
None
See application file for complete search history.

(56) References Cited

U.S. PATENT DOCUMENTS

| | | | |
|---|---|---|---|
| 5,578,480 A | 11/1996 | Khandke | |
| 5,763,205 A | 6/1998 | Hashimoto et al. | |
| 5,773,277 A | 6/1998 | Hashimoto et al. | |
| 5,840,546 A | 11/1998 | Morikawa et al. | |
| 5,939,403 A * | 8/1999 | Maruyama et al. | 514/53 |
| 6,150,115 A | 11/2000 | Miyaura et al. | |
| 6,159,954 A * | 12/2000 | Maruyama et al. | 514/53 |
| 6,184,023 B1 | 2/2001 | Hashimoto et al. | |
| 7,078,217 B2 | 7/2006 | Corcoran et al. | |
| 7,118,902 B2 | 10/2006 | Corcoran et al. | |
| 2004/0044194 A1 | 3/2004 | Corcoran et al. | |
| 2004/0142863 A1 | 7/2004 | Corcoran et al. | |
| 2005/0244399 A1 | 11/2005 | English et al. | |
| 2005/0260733 A1 | 11/2005 | LaVallie et al. | |
| 2006/0233782 A1 | 10/2006 | Gruskin et al. | |
| 2007/0167399 A1 | 7/2007 | Asari et al. | |

FOREIGN PATENT DOCUMENTS

| | | |
|---|---|---|
| JP | 2-57182 | 2/1990 |
| JP | 2004-24189 | 1/2004 |
| JP | 2006-290842 | 10/2006 |
| JP | 3980657 | 7/2007 |
| WO | WO 91/06303 | 5/1991 |
| WO | WO 96/16166 | 5/1996 |
| WO | WO 2004/103299 A2 | 12/2004 |
| WO | 2006/077853 | 7/2006 |

OTHER PUBLICATIONS

JP2006-290842 (Kadomatsu et al., published Oct. 26, 2006) English translation.*
Koltzengurg et al.Curr. Opin. Neurol. 2001, 14: 641-647.*
Sommer Curr. Opin. Neurol. 2003, 16: 623-628.*
Plaas et al. Glycobiology, 2001, 11: 779-790.*
JP2004-024189 English translation.*
NiedertÖst, Barbara P. et al.; "Bovine CNS Myelin Contains Neurite Growth-Inhibitory Activity Associated with Chondroitin Sulfate Proteoglycans"; *The Journal of Neuroscience*, Oct. 15, 1999; 19(20):8979-8989.
Honda, Shizuyuo et al.; "Extracelular ATP or ADP Induce Chemotaxis of Cultured Microglia through $G_{1/o}$-Coupled P2Y Receptors"; *The Journal of Neuroscience*, Mar. 15, 2001; 21(6):1975-1982.
Yamagata, Tatsuya, et al.; "Purification and Properties of Bacterial Chondroitinases and Chondrosulfatases"; *The Journal of Biological Chemistry*; vol. 243; No. 7; Issue of Apr. 10, 1968; pp. 1523-1535.
Hamai, Akio et al.; "Two Distinct Chondroitin Sulfate ABC Lyases"; *The Journal of Biological Chemistry*; vol. 272; No. 14; Issue of Apr. 4, 1997; pp. 9123-9130.

(Continued)

*Primary Examiner* — Chang-Yu Wang
(74) *Attorney, Agent, or Firm* — Kratz, Quintos & Hanson, LLP

(57) ABSTRACT

An object of the present invention is to provide a substance which is able to be an active ingredient for the improvement of dysfunction caused by nerve damage. An improving agent for dysfunction due to nerve damage of the present invention as a means for resolution thereof is characterized in that it comprises an endo-β-N-acetylglucosaminidase type enzyme which hydrolyzes an N-acetylglucosamide bond in a keratan sulfate backbone as an active ingredient. When the improving agent of the present invention is administered, clinical improvement is achieved in motor neuron dysfunction and sensory neuron dysfunction such as neuropathic pain represented by a pain caused by allodynia and hyperalgesic reaction of the object to be treated.

5 Claims, 8 Drawing Sheets

(56) References Cited

OTHER PUBLICATIONS

Nakazawa, Kiyoshi et al.; "Purification of Keratan Sulfate-endogalactosidase and Its Action on Keratan Sulfates of Different Origin"; *The Journal of Biological Chemistry*; vol. 250; No. 3; Issue of Feb. 10, 1975; pp. 912-917.

Basso, D. Michele, et al.; "Graded Histological and Locomotor Outcomes after Spinal Cord Contusion Using the NYU Weight-Drop Device versus Transection"; *Experimental Neurology*; 139;244-256; (1996).

Chaplan, S.R. et al.; "Quantitative assessment of tactile allodynia in the rat paw"; *Journal of Neuroscience Methods*; 53; (1994); 55-63.

Yamagishi, Kiwamu, et al.; "Purification, Characterization, and Molecular Cloning of a Novel Keratan Sulfate Hydrolase, Endo-β-N-acetylglucosaminidase, from *Bacillus circulans*"; *The Journal of bilogical Chemistry*; vol. 278; No. 28; Issue of Jul. 11, 2003; pp. 25766-25772.

*Bacillus circulans* endo-beta-N-acetylglucosaminidase gene, complete cds; GenBank; AY188989.1 (http://www.ncbi.nlm.nih.gov/nuccore/32454884).

Burgess et al., "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue," *The Journal of Cell Biology*, vol. 111, Nov. 1990, pp. 2129-2138.

Bowie et al., "Deciphering the Message in Protein Sequences; Tolerance to Amino Acid Substitutions," *Science*, New Series, vol. 247, No. 4948 (Mar. 16, 1990).

Pawson et al., "Assembly of Cell Regulatory Systems Through Protein Interaction Domains," *Science*, vol. 300 (Apr. 18, 2003), pp. 445-452.

Blight, Andrew R., *Nature Neuroscience Supplement*, vol. 5 (Nov. 2002), pp. 1051-1054.

Schmidt, et al., "Neural Tissue Engineering: Strategies for Repair and Regeneration," *Annu. Rev. Biomed. Eng.* 2003. 5: pp. 293-347.

Hoke, Ahmet, "Mechanisms of Disease: what factors limit the success of peripheral nerve regeneration in humans?," *Nature Clinical Practice Neurology* (Aug. 2006), vol. 2, No. 8, pp. 448-454.

t Hart, et al., "The use of animal models to investigate the pathogenesis of neuroinflammatory disorders of the central nervous system," *Current Opinion in Neurology* (2003), No. 16, pp. 375-383.

Sung, et al.; "A possible role of RhoA/Rho-kinase in experimental spinal cord injury in rat," *Brain Research*, No. 959 (Jan. 3, 2003), pp. 29-38.

Supplemental European Search Report dated Oct. 4, 2011, in European patent application No. 08790747.3.

International Search Report for International Application No. PCT/JP2008/061834 dated Jul. 11, 2008.

Japanese Office Action dated Apr. 9, 2013, in the corresponding Japanese patent application No. 2009-521624.

\* cited by examiner

Keratan sulfate (20 μg/mL)　　　Keratan sulfate (20 μg/mL) + Y27632 (15 μM)

WT ALS① ALS②

SEQUENCE LISTING

<160> NUMBER OF SEQ ID NOS: 1

<210> SEQ ID NO 1
<211> LENGTH: 1936
<212> TYPE: PRT

<213> ORGANISM: Bacillus circulans

<400> SEQUENCE: 1

```
Met Ser Ser Arg Leu Lys Arg Lys Cys Ser Met Leu Leu Thr Phe Thr
1               5                   10                  15

Met Ile Phe Gln Leu Leu Gly Leu Phe Leu Lys Gly Glu Ile Val
            20                  25                  30

Ser Ala Ser Ile Arg Gln Asp Pro Thr Thr Gly Asn Tyr Tyr Lys Asn
            35                  40                  45

Val Pro Leu Val Gly Ala Asp Phe Asp Ala Ser Asn Ser Asn Ile
    50                  55                  60

Val Ala Lys Gly Thr Trp Asp Asp Asn Thr Ala Pro Leu Asn Thr Phe
65                  70                  75                  80

Phe Val Asp Lys Gly Thr Ala Thr Asp Gly Phe Thr Thr Ala Arg
                85                  90                  95

Ile Thr Thr Val Thr Asp Gln Val Tyr Glu Gly Gly Ser Leu Gln Phe
                100                 105                 110

Gly Asp Gly Ser Thr Tyr Pro Ile Asn Leu Asn Tyr Lys Val Asp Gly
            115                 120                 125

Leu Glu Val Gly Ala Thr Tyr Arg Leu Ser Ala Tyr Met Lys Leu Phe
130                 135                 140

Pro Gly Tyr Pro Ala Lys Gly Gly Gln Phe Gly Val Lys Asn His Asp
145                 150                 155                 160

Thr Ala Asn Tyr Thr Thr Gly Gly Glu Thr Lys Ser Val Asn Phe Ser
                165                 170                 175

Thr Val Thr Ala Asp Trp Lys Glu Tyr Ser Val Thr Phe Thr Pro Thr
            180                 185                 190

Tyr Pro His Ala Lys Ile Phe Phe Trp Gly Ser Asn Asn Leu Pro Lys
            195                 200                 205

Val Leu Val Asp Lys Leu Arg Leu Glu Lys Val Leu Glu His Pro Gly
210                 215                 220

Pro Ala Ala Pro Ala Val Thr Ala Asp Asp Val Asn Asn Ile Val Val
225                 230                 235                 240

Gly Ile Asp Glu Thr Met Glu Tyr Asn Ile Asn Gly Ala Gly Trp Val
                245                 250                 255

Ala Tyr Lys Glu Tyr Ala Lys Pro Asp Leu Lys Gly Asp Leu Ile Val
            260                 265                 270

Gln Ile Arg Val Lys Glu Thr Leu Asn Thr Leu Ala Gly Glu Val Thr
            275                 280                 285

Thr Leu Thr Phe Thr Ala Gln Asn Asp Pro Ala Pro Gly Gln Pro Glu
290                 295                 300

Gln Leu Leu Leu Lys Asp Gly Asp Phe Glu Ala Gly Ala Ala Ser Val
305                 310                 315                 320

Thr Thr Asp Thr Asn Val Gln Asn Gln Phe Phe Ser Lys Asn Asn Gln
                325                 330                 335

Tyr Glu Ile Val Thr Gly Asp Thr Ala Ser Gly Gln Tyr Ala Leu Lys
            340                 345                 350

Leu Arg Ser Pro Glu Thr Ile Gly Tyr His Lys Thr Asp Leu Lys Pro
            355                 360                 365

Ser Thr Lys Tyr Gln Ile Ser Phe Met Ala Lys Val Gly Ser Ala Ser
            370                 375                 380

Gln Lys Leu Ser Phe Arg Ile Ser Gly Tyr Lys Asn Asp Asn Pro Tyr
385                 390                 395                 400

Asp Leu Asp Asn Val Met Asn Tyr Ile Glu His Thr Gln Met Lys Asn
```

```
                    405                 410                 415
Thr Gly Trp Ser Arg Phe Tyr Tyr Asp Leu Glu Thr Gly Pro Ser Ala
            420                 425                 430
Thr Ser Ala Phe Ile Asp Phe Ser Thr Ala Ala Gly Ser Thr Ala Trp
            435                 440                 445
Ile Asp Asp Val Lys Leu Val Glu Gln Gly Pro Ala Asp Pro Pro Val
450                 455                 460
Thr Glu Pro Thr Leu Ser Arg Gly Ser Arg Leu Phe Leu Glu Lys Gly
465                 470                 475                 480
Leu Gln Ile Gln Ser Trp Val Pro Thr Asp Val Ala Tyr Ala Thr Arg
                485                 490                 495
Lys Trp Met Lys Pro Pro Thr Ala Glu Glu Ile Val Asp Leu Gly Leu
            500                 505                 510
Thr Thr Val Gln Tyr Asn Asp Ala Pro Asn Tyr Ser Lys Thr Leu His
            515                 520                 525
Glu Glu Tyr Lys Lys Leu Gln Gln Thr Asn Pro Ser Leu Pro Asp Leu
            530                 535                 540
Lys Trp Gly Val Ala Phe Gly Pro Asn Ala Asn His Leu Ser Ser Ser
545                 550                 555                 560
Tyr Phe Asp Ser Glu Thr Ile Ala Lys His Asp Pro Asn Lys Thr Gly
                565                 570                 575
Ala Pro Thr Glu Glu Gln Lys Ala Arg Gly Phe Leu Thr Pro Asp Gln
            580                 585                 590
Leu Ala Asn Val Gln Asn Leu Asn Asn Ile Gly Phe Gly Asp Glu Glu
            595                 600                 605
Asp Tyr Ser Asp Thr Leu Thr Gln Thr Leu Lys Glu Trp Phe Glu Val
            610                 615                 620
Ser Lys Lys His Tyr Pro Asn Val Leu Val His His Asn Glu Val Gly
625                 630                 635                 640
Asn Thr Pro Pro Thr Met Ser Leu Ile Ser Thr Phe Asn Glu Asn
                645                 650                 655
Met Leu Arg Lys Tyr Met Arg Thr Ala Lys Pro Asp Phe Ile Thr Tyr
            660                 665                 670
Asp Met Tyr Tyr Phe Arg Glu Asn Arg Gln Ser Ser Glu Val Gly Gly
            675                 680                 685
Thr Val Ile Pro Phe Tyr Asp Asp Leu Asn Arg Tyr Arg Lys Val Ala
            690                 695                 700
Ser Glu Gly Tyr Asp Gly Ser Gly Leu Ser Pro Ile Pro Phe Gly Thr
705                 710                 715                 720
Tyr Leu Gln Gly Trp Arg Thr Gly Pro Gly Ala Ala Thr Tyr Glu Lys
                725                 730                 735
Arg Gly Asp Gly Trp Tyr Glu Ile Thr Glu Ser Gln Ala Tyr Leu Ser
            740                 745                 750
Ala Phe Ala Asn Trp Thr Phe Gly Ala Lys Trp Leu Ser Met Phe Arg
            755                 760                 765
Trp Ile Glu Asp Thr Pro Gly Tyr Leu Phe Ser Asp Tyr Arg Pro Asp
            770                 775                 780
Glu Asp Gly Asn Trp Pro Lys Tyr His Ile Tyr Gly Gln Tyr Lys Glu
785                 790                 795                 800
Met Phe Arg Gln Ser Lys Asn Leu Gly Glu His Leu Ile Arg Ile Asn
                805                 810                 815
Asn Lys Asp Val Val Ile Val Pro Gly Gln His Met Lys Asp Gly Gln
            820                 825                 830
```

-continued

```
Ile Thr Lys Asn Asn Arg Pro Lys Asp Asn Pro Glu Trp Thr Lys Ser
        835                 840                 845
Gly Asp Arg Ala Phe Ile Asp Ser Leu Glu Ile Ser Asn Leu Gly Lys
    850                 855                 860
Thr Asn His Ser Leu Lys Gly Asp Val Phe Ile Gly Tyr Phe Asp Pro
865                 870                 875                 880
Leu Pro Gly Ile Asp Thr Thr Gln Phe Phe Thr Ser Thr Ala Pro Lys
                885                 890                 895
Tyr Phe Met Leu Leu Asn Gly Leu Thr Ser Gln Gly Leu Pro Ala
                900                 905                 910
Glu Glu Gln Thr Gly Ser Ser Tyr Glu Thr Arg Gln Glu Ile Lys Val
                915                 920                 925
Thr Phe Asp Leu Ser Gly Gly Gln Ala Arg Ala Asp Gln Leu Arg Lys
930                 935                 940
Val Ser Arg Leu Thr Gly Glu Leu Val Ala Ala Pro Leu Lys Asp Leu
945                 950                 955                 960
Gly Asn Gly Lys Tyr Glu Met Thr Val Val Leu Gly Gly Met Ala
                965                 970                 975
Asp Leu Tyr Phe Trp Glu Leu Gly Ser Leu Asn Thr Gly Asn Ser Lys
            980                 985                 990
Pro Val Val Ala Asp Thr Pro His Asp Val Arg Leu Thr Gly Asp Pro
            995                 1000                1005
Lys Tyr Ala Lys Asn Arg Glu Ile Arg Asp Leu Thr Gly Lys Thr
    1010                1015                1020
Val Thr Val Gly Trp Ile Lys Asp Thr Tyr Ser Pro Val Pro Gln
    1025                1030                1035
Pro Leu Ile His Tyr Asn Phe Ser Phe Thr Lys Asp Gln Asn Gly
    1040                1045                1050
Lys Leu Gln Pro Met Lys Asn Pro Asp Ile Leu Ser Tyr Phe Thr
    1055                1060                1065
Arg Tyr Tyr Glu Asn Thr Leu Trp Asn Lys Arg Val Glu Arg Ile
    1070                1075                1080
Gln Lys Glu Ser Asn Val Lys Leu Glu Phe Val Ala Asp Ile Ala
    1085                1090                1095
Trp Thr Lys Gln Glu Leu Met Asp Asn Ile Arg Lys Val Lys Glu
    1100                1105                1110
Gly Gln Thr Val Asp Gly Met Pro Asp Ile Leu Ile Val Pro Asp
    1115                1120                1125
Glu Trp Thr Trp Ser Gly Leu Ile Gln Asn Glu Met Ile Leu Pro
    1130                1135                1140
Ala Ser Ser Phe Ser Glu Phe Asp Phe Thr Glu Arg Lys Trp Asn
    1145                1150                1155
Lys Ser Tyr Lys Ala Met Thr Thr Trp Lys Asp Gln Ile Tyr Gly
    1160                1165                1170
Met Tyr Ala Gly Pro Thr Met Asn Ser Thr Gly Leu Phe Val Asn
    1175                1180                1185
Lys Ala Leu Gln Ala Ser Ile Gly Val Thr Asp Asp Leu Met Ala
    1190                1195                1200
Leu Gln Gln Asn Asn Ala Trp Asp Trp Asn Lys Leu Arg Glu Val
    1205                1210                1215
Ala Ser Ala Phe Gln Ala Ser Ala Asn Arg Glu Gly Lys Tyr Leu
    1220                1225                1230
Leu Ala Gly Thr Asp Glu Leu Phe Lys Gln Met Val Tyr Ala Asn
    1235                1240                1245
```

```
Gly Ala Ala Arg Gly Ser Val Gly Gly Ala Met Asn Gln Glu Phe
    1250                1255                1260

Asp Leu Thr Ser Ser Ser Phe Arg Glu Ala Ala Glu Leu Tyr Ser
    1265                1270                1275

Glu Leu His Ala Ala Gly Leu Ile Ala Ala Lys Pro Glu Gly Ala
    1280                1285                1290

Thr Asp Asp Trp Tyr Val Glu Gln Phe Ser Lys Asn Asn Ile Leu
    1295                1300                1305

Phe Leu Ala Leu Pro Tyr Gln Gln Thr Val Asp Lys Leu Lys Phe
    1310                1315                1320

Ser Tyr Thr Asn Gln Asp Ala Val Ile Glu Met Lys Glu Gly Ser
    1325                1330                1335

Phe Leu Gly Gln Pro Ala Leu Ile Pro Thr Ile Val Asp Ala Tyr
    1340                1345                1350

Glu Thr Ala Tyr Pro Asp Gly Ile Tyr Lys Met Ala Gln Gly Asp
    1355                1360                1365

Trp Val Phe Leu Met Phe Pro Lys Gly Pro Ser Ala Thr Gly Tyr
    1370                1375                1380

Ala Ala Met Ile Asp Asn Pro Ala Tyr Pro Val Leu Leu Ser Ser
    1385                1390                1395

Ser Ala Asn Pro Ala Asp Ala Ala Tyr Val Trp Asn Ile Leu Ser
    1400                1405                1410

His Glu Phe Glu Gly Val Ala Tyr Asp Arg Phe Leu Lys Leu Tyr
    1415                1420                1425

Leu Asn Gln Arg Glu Val Asp Lys Thr Thr Leu Lys Arg Ile Gly
    1430                1435                1440

Leu Lys Glu Gly Val Trp Asp Ser Tyr Ser Gly Thr Gly Ala Trp
    1445                1450                1455

Glu Gln Val Ile Lys Pro Gly Val Leu Pro Met Leu Gln Ala Gly
    1460                1465                1470

Val Ile Asp Glu Ala Lys Leu Ala Glu Leu Ser Val Glu Ala Ala
    1475                1480                1485

Ser Tyr Val Thr Asn Asn Met Thr Lys Pro Ala Gln Pro Gly Glu
    1490                1495                1500

Glu Pro Gly Glu Glu Pro Gly Glu Gln Pro Gly Glu Gln Pro Gly
    1505                1510                1515

Glu Gln Pro Gly Glu Gln Pro Gly Glu Gln Pro Gly Glu Gln Pro
    1520                1525                1530

Gly Glu Gln Pro Gly Glu Gln Pro Gly Glu Gln Pro Gly Ala Gly
    1535                1540                1545

Asn Gly Ser Glu Asn Gln Gly Gly Asn Glu Asp Gln Gly Gly Asn
    1550                1555                1560

Gly Ser Gln Gly Gly Asn Gly Pro Lys Pro Glu Lys Ile Ile Val
    1565                1570                1575

Lys Pro Gly Glu Leu Ile Ala Val Glu Gly Lys Val Thr Ile Val
    1580                1585                1590

Val Pro Ala Gly Ala Thr Glu Ile Val Leu Pro Pro Gln Ala Ala
    1595                1600                1605

Glu Leu Pro Gln Gln His Lys Val Glu Leu Lys Thr Asp Arg Val
    1610                1615                1620

Thr Leu Glu Val Pro Ser Gly Leu Leu Lys Lys Leu Ala Ser Arg
    1625                1630                1635

Ile Ala Asp Lys Asp Val Ser Ile Ser Leu Lys Ala Ala Pro Leu
```

-continued

```
              1640                1645                1650
Thr Ala Ala Gln Ala Lys Asp Ala Ile Ser Lys Asn Lys Ser Val
    1655                1660                1665
Ser Pro Ser Ala Ile Thr Leu Ala Gly Gly Val Tyr Asp Phe Lys
    1670                1675                1680
Leu Ser Ala Ala Gly Ala Asn Gly Ser Tyr Ala Glu Leu Ser Glu
    1685                1690                1695
Phe Asp Gln Pro Ile Thr Ile Ser Leu Lys Ile Glu Ser Gly Val
    1700                1705                1710
Asn Pro Glu Gln Val Gly Ile Tyr Tyr Ile Ser Gly Asn Gly Lys
    1715                1720                1725
Leu Asp Tyr Ile Gly Gly Glu Tyr Arg Asp Gly Glu Leu Ala Ala
    1730                1735                1740
Glu Val Thr His Phe Ser Gln Tyr Ala Val Leu Lys Val Val Lys
    1745                1750                1755
Val Phe Asp Asp Val Pro Ala Gly His Trp Ala Glu Gly Val Ile
    1760                1765                1770
Ser Lys Leu Thr Ser Arg Leu Met Val Asp Gly Thr Ser Glu Thr
    1775                1780                1785
Thr Phe Glu Pro Glu Arg Val Val Thr Arg Ala Glu Phe Thr Ala
    1790                1795                1800
Leu Leu Ala Arg Ala Leu Lys Leu Thr Ala Gly Gly Thr Pro Thr
    1805                1810                1815
Phe Ala Asp Val Lys Ala Gly Asp Trp Tyr Ala Asp Ala Val Thr
    1820                1825                1830
Ala Ala Val Glu Ala Gly Ile Ala Glu Gly Lys Ser Ala Gly Gln
    1835                1840                1845
Phe Glu Pro Gln Ala Arg Ile Thr Arg Glu Glu Met Val Val Met
    1850                1855                1860
Thr Met Arg Ala Tyr Asn Lys Ala Lys Asp Lys Gly Pro Ser Thr
    1865                1870                1875
Gly Val Glu Ala Ser Phe Thr Asp Glu Asn Gln Ile Ser Ala Trp
    1880                1885                1890
Ala Val Glu Gln Val Lys Ala Ala Ala Leu Gln Leu Ile Gln
    1895                1900                1905
Gly Arg Ala Gln Gly Lys Phe Glu Pro Gln Gly Thr Ala Thr Arg
    1910                1915                1920
Ala Glu Ala Val Gln Val Ile Phe Asn Met Leu Leu Lys
    1925                1930                1935
```

METHOD FOR TREATING NEUROPATHIC PAIN

This application is a Divisional Application of prior application Ser. No. 12/667,178 filed on Nov. 23, 2010, now abandoned, which was a 371 National stage application of PCT application JP2008/061834, filed on Jun. 30, 2008, which is hereby incorporated by reference.

TECHNICAL FIELD

The present invention relates to an improving agent for dysfunction due to nerve damage and to an Rho kinase activation inhibitor.

BACKGROUND ART

In human central nervous system (CNS), it is very difficult to regenerate the neuronal axon which was once injured due to spinal cord injury, cerebrovascular disease, cerebral injury or the like and, once a deficit symptom of motor function or sensory function happens, recovery therefrom is difficult whereby one shall suffer from the aftereffects thereof throughout his/her life. That has been well known not only among persons skilled in the art but also among common people and, in recent years, the reasons thereof have been gradually clarified. For the recovery of neural function, there is needed the regeneration of neuronal network by an elongation of neuronal axon cut by injury beyond the injured area resulting in synapse formation connected to the secondary neuron. However, the environment surrounding the central nervous system is equipped with a regeneration inhibiting function via plurality of regeneration suppressing factors for neuronal axons for preventing the disordered formation of synapse and this function disturbs the regeneration of neuronal network. Chondroitin sulfate proteoglycan has been known as one of the regeneration suppressing factors for neuronal axon and has been reported to inhibit the axonal regeneration in the injured area (refer, for example, to Non-Patent Literature 1). Further, in Patent Literature 1, the fact that keratan sulfate plays an important role in the formation of glial scar inhibiting the axonal regeneration is clarified by an experiment in brain-injured model using mice where N-acetylglucosamine 6-O-sulfotransferase 1 (GlcNAc6ST-1) gene which is necessary for biosynthesis of keratan sulfate in the brain is knocked out. In the same document, it is proposed that substances which inhibit the synthesis and the physiological activity of keratan sulfate are effective for the prevention and the treatment of nerve damage from the experimental results that non-expression of keratan sulfate in the injured area results in the suppression of the formation of glial scar.

Further, expression of neuropathic pain is exemplified as a symptom which greatly lowers the QOL (quality of life) among sensory neuron dysfunction. Neuropathic pain is a pain caused by disorder of the central nerve or the peripheral nerve and examples thereof include spontaneous pain, hyperalgesic reaction where the threshold for invasive stimulation lowers and mechanical allodynia where non-invasive mechanical stimulation and tactile stimulation which usually do not induce the pain are erroneously recognized as sharp pain. Examples of the diseases expressing neuropathic pain include cerebral disorder, multiple sclerosis and spinal cord injury as central ones and diabetes mellitus and herpes zoster as peripheral ones. Among neuropathic pains, allodynia is characterized in that intractable and burning pain and piercing pain continue for a long period of time without intermittence and is also a cause of the reduction in the effect of rehabilitation due to the pain. There has been almost no satisfactory drug therapy for neuropathic pain and there has been a demand for the development of drugs which satisfy both pharmaceutical effect and safety. However, the development of the drug has been unable to make satisfactory progress. One of the reasons therefor is that it is thought that the mechanism of pathogenesis is not single but many of them are entangled in a complicated manner. Details of the onset mechanism for allodynia is still ambiguous even at this time but, in recent years, findings for ATP (adenosine triphosphate) which has been known as a pain-causing substance have started to be reported. It has been gradually aware of that ATP strongly activates spinal microglia and causes potentiation of production of various mediators assisting the abnormal neuronal network formation, synapse transportation and release of neurotransmitters with re-construction of cell skeleton whereby it participates in neuropathic pain, and ATP as such also activates Rac which is one of an Rho family (Non-Patent Literature 2).

It has been also being aware of that spinal microglia of dorsal horn is activated by nerve injury and that stimulation of P2X4 receptor which is strongly expressed therein causes neuropathic pain, and it has been proposed of the participation of Rho kinase signal transduction system as one of the routes of cascade of the activation as such (Non-Patent Literature 2).

Patent Literature 1: JP-A-2006-290842

Non-Patent Literature 1: Niederost, B. P., Zimmermann, D. R., Schwab, M. E. & Bandtlow, C. E. Bovine CNS myelin contains neurite growth-inhibitory activity associated with chondroitin sulfate proteoglycans. *J. Neurosci.* 19, 8979-8989 (1999).

Non-Patent Literature 2: Honda, S. et al., 2001. Extracellular ATP or ADP Induce Chemotaxis of Cultured Microglia through Gi/o-Coupled P2Y Receptors. *J. Neurosci.* 21(6), 1975-1982.

DISCLOSURE OF THE INVENTION

Problems to be Solved by the Invention

As above-mentioned, research and development for the prevention and the treatment of nerve damage have been eagerly carried out day to day but, unfortunately, no satisfactory results have been achieved yet at present. In fact, as above-mentioned, although there is a proposal in the Patent Literature 1 that substances which inhibit the synthesis and the physiological activity of keratan sulfate are effective for the prevention and the treatment of nerve damage, no result where specific substances are actually effective has been available yet.

Under such circumstances, an object of the present invention is to provide a substance which is able to be an active ingredient for the improvement of dysfunction caused by nerve damage.

Means for Solving the Problems

In view of the above, the present inventors have carried out intensive studies and, as a result, they have found that an endo-β-N-acetylglucosaminidase type enzyme which is one of the keratan sulfate degrading enzymes and hydrolyzes an N-acetylglucosaminide bond in a keratan sulfate backbone improves dysfunction due to nerve damage such as motor neuron dysfunction or sensory neuron dysfunction (such as neuropathic pain represented by a pain caused by allodynia and hyperalgesic reaction) and that such an action is mediated by the suppression of an Rho kinase activation by keratan sulfate.

The present inventors have now achieved an idea that, when an endo-β-N-acetylglucosaminidase type enzyme which hydrolyzes an N-acetylglucosaminide bond in a keratan sulfate backbone (hereinafter, it will be sometimes referred to as "an endo-β-N-acetylglucosaminidase type keratan sulfate degrading enzyme") is continuously administered to the injured area of an individual immediately after nerve damage, the spinal cord injury happens for example, so as to remove a keratan sulfate backbone of keratan sulfate proteoglycan, that releases the continuous abnormal activation of nerve cells and non-nerve cells such as glia cell caused by proteoglycan and results in the release of an abnormal axonal guidance function by proteoglycan and also in the therapeutic effect for neuropathic pain. On the basis of the idea as such, the present inventors have for the first time found that, when an endo-β-N-acetylglucosaminidase type keratan sulfate degrading enzyme is continuously administered to the injured area in the intrathecal cavity of model rats for spinal cord injury, improvement of motor neuron function and sensory neuron function is promoted and that, particularly due to the improvement of the latter, neuropathic pain, particularly allodynia, is able to be improved.

An improving agent for dysfunction due to nerve damage of the present invention achieved by the above-mentioned finding (hereinafter, it will be sometimes referred to as an improving agent of the present invention) is characterized in that, as mentioned in claim 1, it comprises an endo-β-N-acetylglucosaminidase type enzyme which hydrolyzes an N-acetylglucosaminide bond in a keratan sulfate backbone as an active ingredient.

The improving agent mentioned in claim 2 is characterized in that, in the improving agent mentioned in claim 1, the nerve damage is that arising from spinal cord injury.

The improving agent mentioned in claim 3 is characterized in that, in the improving agent mentioned in claim 1, the nerve damage is amyotrophic lateral sclerosis.

The improving agent mentioned in claim 4 is characterized in that, in the improving agent mentioned in any of claims 1 to 3, the dysfunction due to nerve damage is motor neuron dysfunction.

The improving agent mentioned in claim 5 is characterized in that, in the improving agent mentioned in any of claims 1 to 3, the dysfunction due to nerve damage is sensory neuron dysfunction.

The improving agent mentioned in claim 6 is characterized in that, in the improving agent mentioned in claim 5, the sensory neuron dysfunction is neuropathic pain.

The improving agent mentioned in claim 7 is characterized in that, in the improving agent mentioned in claim 6, the neuropathic pain is a pain caused by allodynia or hyperalgesic reaction.

As mentioned in claim 8, an improving agent for neuropathic pain of the present invention is also characterized in that, it comprises an endo-β-N-acetylglucosaminidase type enzyme which hydrolyzes an N-acetylglucosaminide bond in a keratan sulfate backbone as an active ingredient.

As mentioned in claim 9, an Rho kinase activation inhibitor of the present invention (hereinafter, it will be sometimes referred to as an inhibitor of the present invention) is characterized in that, it comprises an endo-β-N-acetylglucosaminidase type enzyme which hydrolyzes an N-acetylglucosaminide bond in a keratan sulfate backbone as an active ingredient.

Further, as mentioned in claim 10, an agent for treating nerve damage of the present invention comprising an endo-β-N-acetylglucosaminidase type enzyme which hydrolyzes an N-acetylglucosaminide bond in a keratan sulfate backbone as an active ingredient for a continuous administration to a neuropathic site at the dose of 0.3 milliunit (mU) to 15000 mU per day to an adult human.

Effect of the Invention

In accordance with the present invention, an endo-β-N-acetylglucosaminidase type keratan sulfate degrading enzyme is provided as an active ingredient for an improving agent for dysfunction of motor neuron and of sensory neuron due to nerve damage such as spinal cord injury or, to be more specific, for an improving agent for neuropathic pain for example. There is also provided an agent for administering to nerve damage for a continuous administration to a neuropathic site, which comprises a specific amount of an endo-β-N-acetylglucosaminidase type keratan sulfate degrading enzyme.

BEST MODE FOR CARRYING OUT THE INVENTION

Figure 1:
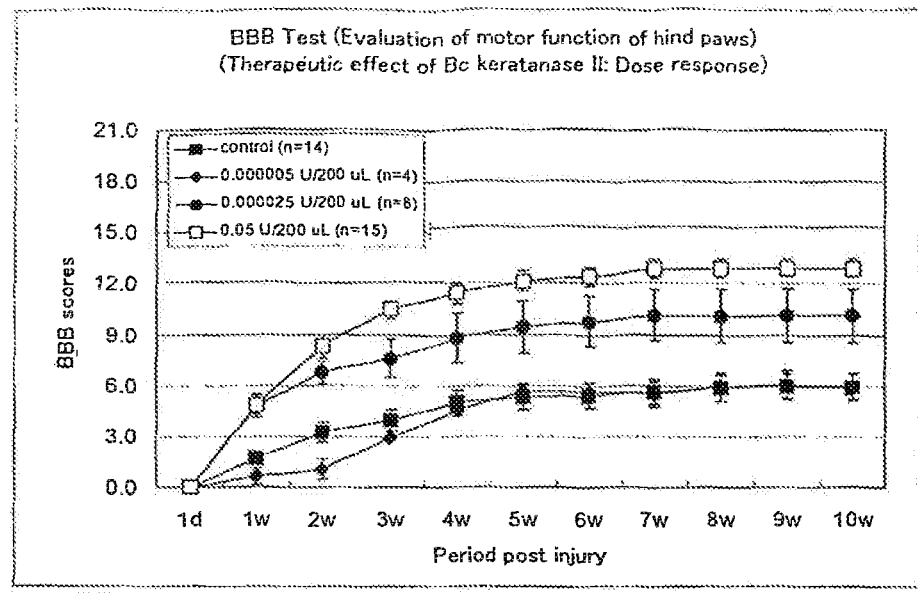
FIG. 1 Experimental Result of Example 1, No. 1: This is a graph showing the dose response of the therapeutic effect in an evaluation of the recovery of hind paw motor function (BBB Test) of Bc keratanase II.

An improving agent of the present invention is characterized in that the agent comprises an endo-β-N-acetylglucosaminidase type enzyme which hydrolyzes an N-acetylglucosaminide bond in a keratan sulfate backbone (an endo-β-N-acetylglucosaminidase type keratan sulfate degrading enzyme) as an active ingredient. The endo-β-N-acetylglucosaminidase type enzyme which hydrolyzes an N-acetylglucosaminide bond in a keratan sulfate backbone is a keratan sulfate degrading enzyme, also known as keratanase II, and the enzyme per se is a known substance (hereinafter, the endo-β-N-acetylglucosaminidase type enzyme which hydrolyzes an N-acetylglucosaminide bond in a keratan sulfate backbone will be abbreviated as keratanase II). Keratanase II is an enzyme derived from microbes and has been known to be produced by Ks36 strain of bacteria belonging to genus *Bacillus* (Accession Number for the microbe: FERM P-10204) (refer, if necessary, to Japanese Patent No. 2726274; hereinafter, keratanase II produced by Ks36 strain will be abbreviated as Ks36 keratanase II). A heat resistant keratanase II having an excellent stability against heat where the optimum reaction temperature is 50 to 60° C. has been known as well and the enzyme has been known to be produced by *Bacillus circulans* KsT202 strain (Accession Number for the microbe: FERM BP-5285) (hereinafter, the heat resistant keratanase II will be abbreviated as Bc keratanase II). Bc keratanase II is characterized in that it degrades keratan sulfate whereupon sulfated keratan sulfate disaccharide and keratan sulfate tetrasaccharide are mainly produced (refer, if necessary, to Japanese Patent No. 3734504, U.S. Pat. No. 5,840,546, European Patent No. 0798376 B1, etc.). Bc keratanase II may be a genetically recombinant type heat resistant keratanase II which is produced, for example, by transferring the heat resistant keratanase II gene cloned from *Bacillus circulans* KsT202 strain to a host such as *Escherichia coli* (refer, if necessary, to JP-A-2004-24189 and Gen Bank: Accession No. AY188989 hereinafter, genetically recombinant type heat resistant keratanase II will be abbreviated as rBC keratanase II). The total amino acid sequence of rBC keratanase II described in the above-mentioned JP-A-2004-24189 is attached hereto as SEQ ID No. 1.

Although both Ks36 keratanase II and Bc keratanase II are the endo-β-N-acetylglucosaminidase type enzymes, they are different in terms of reactivity to high concentrated keratan polysulfate (keratan sulfate having a high degree of sulfation), optimum pH, pH stability, optimum temperature, temperature stability, influence of inhibition by drugs, etc. and, therefore, they are essentially different enzymes (refer, if necessary, to Japanese Patent No. 3734504, U.S. Pat. No. 5,840,546, European Patent No. 0798376 B1, etc.). As to the enzyme for an active ingredient of an improving agent for dysfunction due to nerve damage of the present invention, those two kinds of enzymes are advantageously listed wherein Bc keratanase II is preferred and rBC keratanase II is more preferred.

Incidentally, keratanase II used in the present invention is not limited to the above-mentioned exemplified enzymes so far as it is an endo-β-N-acetylglucosaminidase type enzyme which hydrolyzes an N-acetylglucosaminide bond in a keratan sulfate backbone and, further, there is no limitation for the origin and the enzymatic properties thereof.

Keratanase II improves motor neuron dysfunction and sensory neuron dysfunction caused by various nerve damages such as nerve damage arising from spinal cord injury or amyotrophic lateral sclerosis, and the action as such is mediated by the suppression of an Rho kinase activation by keratan sulfate. Rho kinase (ROCK) is a small GTPase (guanosine triphosphate phosphatase) existing in cytoplasm and having an activity of hydrolyzing GTP (guanosine triphosphate) and is an important enzyme for phosphorylation which conducts various controls for cell shape and locomotion by controlling an actin cytoskeletal system or tubulin. This enzyme was found in 1990s and is activated by several intracellular factors such as Rho. When an Rho kinase signal transduction system is activated, an actin cytoskeletal system is inactivated and, as a result, an axonal regeneration is inhibited and decay of growth cone is induced. The facts that the inhibition of the axonal regeneration induced by keratan sulfate is associated with an Rho kinase activation and that an improving action of keratanase II for dysfunction due to nerve damage is mediated by the suppression of the Rho kinase activation have been firstly found by the present inventors and, on the basis of such findings, the present invention provides a novel improving agent for dysfunction due to nerve damage wherein the control of the Rho kinase signal transduction system is a concept.

Keratanase II such as Ks36 keratanase II or Bc keratanase II which is an active ingredient for an improving agent of the present invention or an inhibitor of the present invention (hereinafter, both agents will be sometimes referred to as the drug of the present invention) is made into a parenteral preparation by a common method same as in the case of common parenteral enzyme preparations, parenterally administered to mammals (such as humans, non-human primates, rats, mice, rabbits, cattles, horses, pigs, dogs or cats) by an administration route corresponding to object disease and used for the treatment or the prevention of the aimed disease of the animal.

Examples of the parenteral preparation include liquid preparation (such as solution preparation, suspension preparation, eye drop, nose drop or locally infusion agent to brain, intrathecal cavity, skin, etc.), solid preparation (such as freeze-dried preparation, powder preparation, granule preparation, microcapsule, liposome or liposphere) and semisolid preparation (such as ointment). When the drug of the present invention is manufactured as liquid preparation for example, it is able to be manufactured by dissolving or dispersing keratanase II of a pharmaceutically acceptable grade into a solution to which water for injection, pharmaceutically acceptable additives or carriers such as isotonizing agent (e.g., sodium chloride, potassium chloride, glycerin, mannitol, sorbitol, boric acid, borax, glucose or propylene glycol), buffer agent (e.g., phosphate buffer, acetate buffer, borate buffer, carbonate buffer, citrate buffer, Tris buffer, glutamate buffer or ε-aminocaproate buffer), preservative (e.g., p-hydroxybenzoate, chlorobutanol, benzyl alcohol, benzalkonium chloride, sodium dehydroacetate, sodium edetate, boric acid or borax), nonionic surfactant (e.g., polyoxyethylene sorbitan fatty acid ester, polyoxyethylene hydrogenated castor oil, sucrose fatty acid ester or polyoxyethylene polyoxypropylene glycol), thickener (e.g., polyvinyl alcohol), stabilizer/activity retainer (e.g., serum albumin, gelatin, sucrose, polyethylene glycol, dextran, lactose, maltose, mannitol, xylitol, sorbitol, inositol, sodium edetate, sodium citrate or ascorbic acid), pH adjusting agent (e.g., hydrochloric acid, sodium hydroxide, phosphoric acid or acetic acid), solubilizing aid, antioxidant or substance effective for prevention of adsorption with container are appropriately added. It is also possible that such liquid preparation is dried by a drying method (such as freeze-drying) which does not affect the pharmacological function of keratanase II such as activity whereupon solid preparation which is a type being dissolved before use is prepared. Specific example thereof is that keratanase II of a pharmaceutically acceptable grade is dissolved or suspended in physiological saline, water for injection, isotonic liquid, oily liquid or the like to prepare liquid preparation.

The drug of the present invention prepared as such is administered by an administering method depending upon object disease, degree of symptom, subject to be administered, etc. whereby dysfunction caused by nerve damage is able to be improved, treated or prevented. An example thereof is a method where it is locally administered to the site suffering from nerve damage or surroundings thereof and such a method is preferred. To be more specific, it is possible to conduct a continuous administration to subarachnoid cavity (intrathecal administration) by an osmotic pressure pump using a microtube and such a continuous administration is preferred when an object of the present invention is taken into consideration.

Dose and administering period of the drug of the present invention is to be appropriately determined by medical specialists such as a medical doctor taking the conditions such as object disease, animal species, age or body weight to be administered, degree of symptom or health condition of the subject into consideration and there is no particular limitation provided that the dose and the period are effective for suppressing an activation of Rho kinase in diseased site or for degrading a keratan sulfate backbone of keratan sulfate proteoglycan in glial scar.

Daily dose for intrathecal administration of an improving agent of the present invention to a rat (body weight: 0.3 kg; cerebrospinal fluid amount: 0.3 mL) of a spinal cord-injured model is about 1.5 microunit (μU) (0.000025 U/200 μL) to 30 milliunit (mU), preferably about 0.3 mU (0.005 U/200 μl) to 10 mU, and most preferably about 3.0 mU (0.05 U/200 μL) in terms of enzyme unit of keratanase II. "U/200 μL" in the parentheses means a concentration and an enzyme liquid preparation having each concentration is administered in a dose of 12 μL per day.

When this is converted to an adult human (body weight: 60 kg; cerebrospinal fluid amount: 150 mL) with a presumption that body weight and cerebrospinal fluid amount of a rat are 0.3 kg and 0.3 mL, respectively, it is about 200 times on the basis of body weight while, when it is converted on the basis of cerebrospinal fluid amount by taking the direct intrathecal administration into consideration, it is about 500 times. Accordingly, the dose to an adult human (body weight in average: 60 kg; cerebrospinal fluid amount in average: 150 mL) is as follows.

Thus, the daily dose for intrathecal administration in terms of a conversion based on body weight is about 0.3 mU to 6000 mU, preferably about 60 mU to 2000 mU, and most preferably about 600 mU.

Then the daily dose for intrathecal administration in terms of a conversion based on cerebrospinal fluid amount is about 0.75 mU to 15000 mU, preferably about 150 mU to 5000 mU, and most preferably about 1500 mU.

Accordingly, when the above-mentioned converting methods are considered as a whole, the daily dose for intrathecal administration is about 0.3 mU to 15000 mU, preferably about 60 mU to 5000 mU, and most preferably about 600 mU to 1500 mU.

The administering period is to be decided by medical specialists such as a medical doctor depending upon the symptoms taking expressed amount of keratan sulfate proteoglycan in the injured area and possibility of adverse event, etc. into consideration and a yardstick thereof in the case of a continuous administration is up to about eight weeks, preferably up to about four weeks, and more preferably up to about two weeks after the injury. Time for starting the administration is preferred to be immediately after the injury or three days to about one week after the injury.

Since the preferred specific activity of keratanase II which is an active ingredient is about 2 U/mg protein or higher, the above-mentioned daily dose for intrathecal administration is that about 0.3 mU, 15000 mU, 60 mU, 5000 mU, 600 mU and 1500 mU correspond to not more than about 0.15 microgram (μg), not more than about 7500 μg, not more than about 30 μg, not more than about 2500 μg, not more than about 300 μg and not more than about 750 μg, respectively in terms of the weight of enzyme protein. One unit (1 U) of enzyme amount is defined as enzyme amount producing reducing terminal corresponding to 1 μmol of galactose per minute when a reaction is conducted at 37° C. for 10 minutes using keratan polysulfate derived from cartilage of shark as a substrate (refer, if necessary, to JP-A-2004-24189).

The enzyme amount or the concentration per unit preparation of the drug of the present invention is set depending upon the above-mentioned dose and the preparation is not always necessary to make the enzyme amount or the concentration upon the administration but, for example, dilution may be conducted immediately before the administration or upon the administration to an effective and safe concentration by using diluent. Accordingly, the present invention also provides a kit in which such diluent is combined with the above-mentioned drug of the present invention.

Since the drug of the present invention is medicament with an object of administration to human body, etc., it is preferred that keratanase II which is an active ingredient is in a pharmaceutically acceptable grade and that impurities such as endotoxin, nucleic acid or protease derived from the microbes wherefrom the present enzyme is produced are to be removed as much as possible. Amounts of endotoxin, nucleic acid and protease are to be not more than the detecting limit by the conventional analytic method. For example, with regard to endotoxin, its amount is preferred to be not more than 5.0 pg/100 U when measured by Toxicolor (registered trade mark) System of Seikagaku Corporation. With regard to nucleic acid, it is preferred to be not more than the detecting limit when measured by Threshold Method (DNA measuring device: Threshold (manufactured by Molecular Devices)). With regard to protease, its amount is preferred to be not more than 0.1% to the total protein when measured by using FITC-casein as a substrate.

The improving agent of the present invention is used for improvement, treatment or prevention of dysfunction caused by acute disorder, subacute disorder or chronic disorder of central nerve system (CNS) including spinal cord and brain or peripheral nerve system. Examples of the object disease for the improving agent of the present invention include nerve injury, neural degenerative disorder or neural dysfunction including contusion of central nerve, traumatic brain injury, other brain injury, apoplexy, amyotrophic lateral sclerosis (ALS), multiple sclerosis (MS), brachial plexus injury, ambliophia, spinal cord injury, Alzheimer's disease, Parkinsonism, although it is not limited thereto. Spinal cord injury includes disease such as crush of neuron and traumatic injury caused by traffic accident, accidental fall, contusion, gunshot wound and other injury. When the improving agent of the present invention is administered, clinical improvement is achieved in motor neuron dysfunction (such as motor function disorder of the four limbs and the trunk caused by dysfunction, disorder and paralysis of motor neuron) and sensory neuron dysfunction such as neuropathic pain represented by a pain caused by allodynia and hyperalgesic reaction (such as hypertarachia, dysesthesia, numbness of the four limbs, facial nerve paralysis, etc. caused by dysfunction, disorder and paralysis of sensory neuron) of the object to be treated (patient).

It is also possible that the drug of the present invention is used for the treatment together with other drug which has been known to have an improving effect for nerve damage such as spinal cord injury.

An example of such a drug is that which comprises chondroitinase having an action of degrading chondroitin sulfate proteoglycan as an active ingredient.

Chondroitinase is a lyase which degrades chondroitin sulfate into an unsaturated disaccharide in an eliminating manner. Examples of the enzyme which is available at present will be listed below.

Chondroitinase ABC (derived from *Proteus vulgaris*; sold by Seikagaku Biobusiness Corporation)
Chondroitinase AC I (derived from *Flavobacterium heparinum*; sold by Seikagaku Biobusiness Corporation)
Chondroitinase AC II (derived from *Arthrobacter aurescens*; sold by Seikagaku Biobusiness Corporation)
Chondroitinase AC II (derived from *Flavobacterium* sp. Hp 102)
Chondroitinase B (derived from *Flavobacterium heparinum*; sold by Seikagaku Biobusiness Corporation)
Chondroitinase C (derived from *Flavobacterium* sp. Hp 102)
Chondroitinase AC (recombinant, derived from *Flavobacterium heparinum*; sold by IBEX Technologies Inc.)
Chondroitinase B (recombinant, derived from *Flavobacterium heparinum*; sold by IBEX Technologies Inc.)

Chondroitinase ABC [EC 4.2.2.20 or EC 4.2.2.4] is an enzyme which cleaves an N-acetylhexosaminide bond of glycosaminoglycan containing chondroitin sulfate in an elimination reaction manner whereupon an unsaturated disaccharide having a Δ4-hexuronic acid residue in a non-reducing terminal is mainly produced. It is an enzyme strongly catalyzing the degradation of chondroitin sulfate A derived from cartilage of mammals (containing abundant chondroitin-4-sulfate), chondroitin sulfate C derived from cartilage of shark (containing abundant chondroitin-6-sulfate) and chondroitin sulfate B (dermatan sulfate) derived from skin of mammals while weakly catalyzing the degradation of hyaluronic acid, and it also degrades chondroitin sulfate A, dermatan sulfate and chondroitin sulfate C in a chondroitin sulfate side chain of chondroitin sulfate proteoglycan (Yamagata, T. et al., *J. Biol. Chem.*, 243: 1523-1535 (1968); Hamai A. et al., *J. Biol. Chem.* 272: 9123-9130 (1997)). This enzyme is commercially available as a reagent for the research in, for example, removal of mucopolysaccharide from animal tissue or identification of mucopolysaccharide in the tissue, as an enzyme product produced by bacteria such as *Proteus vulgaris* from Seikagaku Biobusiness Corporation with a code number 100330 (Chondroitinase ABC (*Proteus vulgaris*)) and code number 100332 (Chondroitinase ABC Protease Free (*Proteus vulgaris*)). In addition, an enzyme which is purified in higher purity (being a single protein containing no endotoxin, nucleic acid, contaminating proteins, etc.) having very high specific activity is more preferred since it has been subjected to a clinical test as a treating agent for disc herniation and has been fully clarified for its action to living body. Particularly, the chondroitinase ABC having high purity and high specific activity described in Japanese Patent No. 3980657, U.S. Pat. No. 6,184,023, U.S. Pat. No. 5,773,277, and U.S. Pat. No. 5,763,205, etc. is most preferred. Incidentally, the above chondroitinase ABC is the same enzymes as the following enzymes having other names.

Chondroitinase ABC Type 1
Chondroitin ABC endolyase 1
Chondroitin ABC lyase I
Chondroitin sulfate endolyase
Chondroitin ABC eliminase Gene of the above-mentioned substance having a chondroitinase ABC activity has been cloned and amino acid sequence of the protein and DNA base sequence coding therefor have been also identified (U.S. Pat. No. 5,578,480, JP-A-2007-520447 (WO 2004/103299)). As to the representative amino acid sequence, that which is described in U.S. Pat. No. 5,578,480 may be exemplified. This amino acid sequence comprises 1021 amino acid residues in which amino acids of 1 to 24 constitute a signal sequence and a mature protein comprises 997 amino acid residues (amino acids of 25 to 1021). As to another representative amino acid sequence, that which is described in the database for amino acid sequences (UniProtKB/Swiss-Prot: Entry name CABC_PROVU, Primary accession number P59807, Protein name Chondroitin ABC endolyase 1 [Precursor]) may be exemplified. Although this amino acid sequence also comprises 1021 amino acid residues, it is different in two amino acids from the amino acid sequence described in U.S. Pat. No. 5,578,480 (No. 694: Q→E, No. 738: D→N). In addition, although amino acid sequence described in SEQ ID NO: 1 of US 2006/0233782 A1 is of a mature protein whereby it comprises 997 amino acid residues, it is different in four amino acids from amino acids of 25 to 1021 in the amino acid sequence described in U.S. Pat. No. 5,578,480 (No. 154: A→T, No. 295: I→T, No. 694: Q→E, No. 738: D→N). Thus, even when an enzyme is that where at least four amino acids (such as Nos. 154, 295, 694 and 738) are substituted with other amino acids based on the amino acid sequence described in U.S. Pat. No. 5,578,480, that is still able to be regarded as an enzyme having the identical chondroitinase ABC activity.

It is also possible that the drug where the improving agent of the present invention is made into a pharmaceutical preparation is used for the treatment together with other drug which has been known to have an improving effect for neuropathic pain. Examples of the other drug as such include NSAIDs, opioid and adjuvant analgesics as exemplified below. Thus, examples of opioid analgesic include morphine, fentanyl, oxycodone, codeine phosphate, pethidine, buprenorphine, tramadol, pentazocine and butorphanol. Examples of adjuvant analgesics include a tricyclic type (such as amitriptyline or nortriptyline), a tetracyclic type (such as Tetramide), SSRI (such as paroxetine or fluvoxamine and SNRI (milnacipran) which are antidepressants; examples of anticonvulsant include carbamazepine, lamotrigine, zonisamide, valproic acid and clonazepam; examples of antispasmodic include baclofen; examples of antiarrhythmic include lidocaine and mexiletine; examples of NMDA receptor antagonist include ketamine, dextromethorphan, amantadine and ifenprodil; and examples of a preparation containing an extract from the inflamed skin of rabbit inoculated with vaccinia virus include Neurotropin. Calcium channel blocker (bonding to α2δ subunit) which has been receiving public attention recently such as gabapentin (anticonvulsant) and pregabalin may be also listed. It is also possible to use together with a drug having an antiinflammatory action such as steroidal agent (e.g., methylprednisolone sodium succinate, dexamethasone and betamethasone) or fasudil which is an Rho kinase inhibitor.

EXAMPLES

The present invention will now be more specifically illustrated by way of the following Examples, although the present invention should not be interpreted by limiting to the following description.

Example 1

Improving Action of Keratanase II for Dysfunction after Spinal Cord Injury (Experimental Method)

S. D. Rats (Nippon SLC; female; 9 weeks age) were used in this study. The animals were anesthetized with ether and ketamine cocktail, the ninth and the twelfth thoracic vertebrae were laminectomized and induced spinal cord injury on the ninth thoracic vertebra by means of contusion where IH-0400 Impactor was used. After the injury, small incision was done to dura mater of the twelfth thoracic vertebra and a microtube was inserted into the subarachnoid cavity under a surgical microscope. An osmotic pressure pump (Alzet Osmotic Pump) in which a test sample was previously filled was connected to the microtube. The tube and the pump were sutured to the interspinal ligament and the muscle. Afterward, the muscles and skin were closed in layers. After the operation, all animals were orally given antibiotics for two weeks. The bladder was compressed by manual abdominal pressure once a daily until bladder function restored. The test sample was continuously administered intrathecally for 14 days since the stage of immediately after the injury (administering rate: 12 μL/24 hours; total dose: 168 μL/14 days). The test sample was the following five types.

(1) Bc keratanase II (a heat resistant keratanase II produced by the bacteria of the species *Bacillus circulans* KsT202 strain described in Japanese Patent No. 3734504) (0.000005 U/200 μL, 0.000025 U/200 μL and 0.05 U/200 μL)

(2) Ks36 keratanase II (keratanase II produced by Ks36 strain of bacteria belonging to genus *Bacillus* described in Japanese Patent No. 2726274) (0.000025 U/200 μL, 0.0005 U/200 μL and 0.05 U/200 μL)

(3) Inactivated Bc keratanase II (an enzyme prepared by inactivation of the enzymatic activity of Bc keratanase II (0.05 U/200 μL) at 100° C. (for 10 minutes))

(4) Ps keratanase (although it is an enzyme which degrades keratan sulfate, it is an endo-β-galactosidase type enzyme derived from *Pseudomonas* sp strain which hydrolyzes a β-galactoside bond of non-sulfated galactose of keratan sulfate; hereinafter, it will be referred to as Ps keratanase; refer, if necessary, to the reference document by Kiyoshi Nakazawa and Sakaru Suzuki, *J. Biol. Chem.*, 250:(3) 912-917 (1975), Purification of Keratan sulfate-endogalactosidase and Its Action on Keratan Sulfate of Different Origin) (0.05 U/200 μL).

(5) Physiological saline (200 μL; control)

Experimental Result 1: Evaluation of Motor Neuron Function of Hind Paws (BBB Test)

One day after the injury and once a week from one week after the injury until 10 weeks thereafter, motor neuron function of hind paws was evaluated by using Basso-Beattie-Bresnahan (BBB) scale in accordance with a method of Basso, et al. (Basso, D. M., Beattie, M. S. & Bresnahan, J. C., Graded histological and locomotor outcomes after spinal cord contusion using the NYU weight-drop device versus transection. *Exp. Neurol.*, 139, 244-256 (1996)). The test was conducted under the blind manner by two observers and the quantification was expressed in terms of the value which was an average of the results of two observers. The result is shown in FIG. 1 to FIG. 5.

As will be apparent from FIG. 1, significant recovery of motor neuron function of hind paws was noted in the groups to which Bc keratanase II was administered in an amount of 0.05 U/200 μL and 0.000025 U/200 μL as compared with the group to which physiological saline was administered. Among the above, an effect in the group to which 0.05 U/200 μL was administered was excellent.

Figure 2:
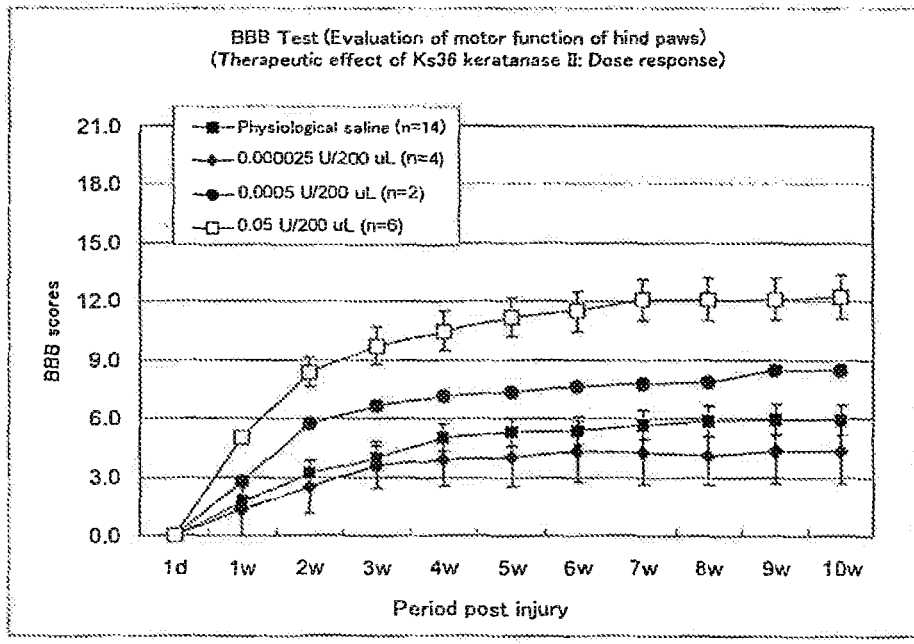
FIG. 2 (the same as above): This is a graph showing the dose response of the therapeutic effect of Ks36 keratanase II.

As will be apparent from FIG. 2, significant recovery of motor neuron function of hind paws was noted in the groups to which Ks36 keratanase II was administered in an amount of 0.05 U/200 μL, and 0.0005 U/200 μL as compared with the group to which physiological saline was administered. Among the above, an effect in the group to which 0.05 U/200 μL was administered was excellent.

Figure 3:
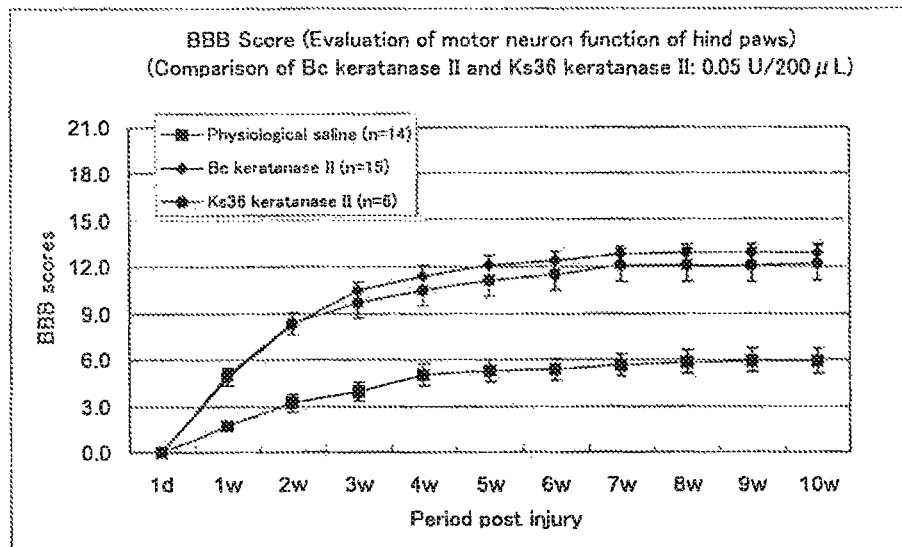
FIG. 3 (the same as above): This is a graph showing the comparison in the therapeutic effects by Bc keratanase II and Ks36 keratanase II when the administered concentration is 0.05 U/200 μL.

As will be apparent from FIG. 3, the effects for the recovery of motor neuron function of hind paws by Bc keratanase II and Ks36 keratanase II were identical when the administered concentration was 0.05 U/200 μL.

Figure 4:
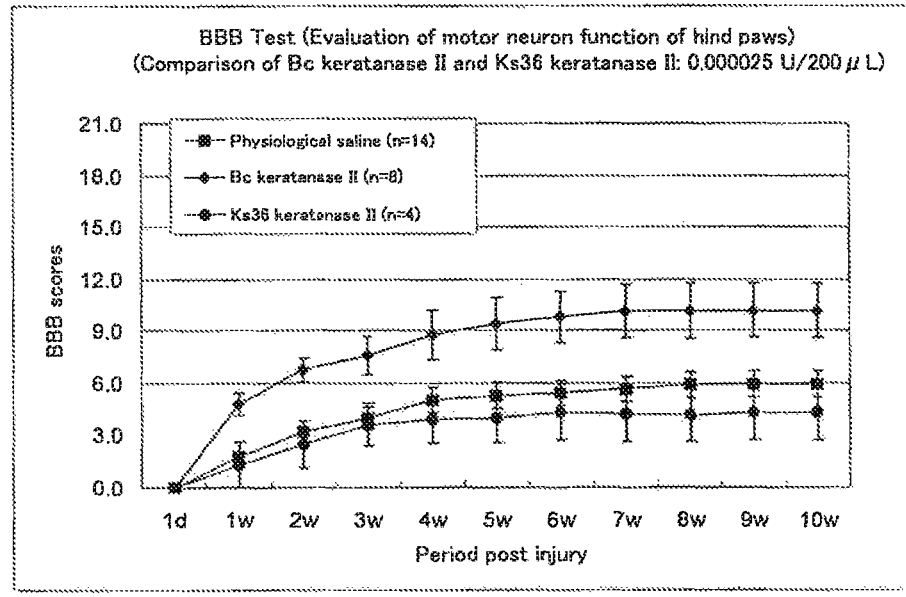
FIG. 4 (the same as above): This is a graph showing the comparison in the therapeutic effects by Bc keratanase II and Ks36 keratanase II when the administered concentration is 0.000025 U/200 μL.

As will be apparent from FIG. 4, when the administered concentration was as low as 0.000025 U/200 μL, the effect for the recovery of motor neuron function of hind paws was noted in Bc keratanase II having an excellent heat stability but it was not noted in Ks36 keratanase II. From such results, it has now become clear that, due to its excellent stability, Bc keratanase II exhibits the efficacy in lower dose and is a better treating agent than Ks36 keratanase II.

Figure 5:
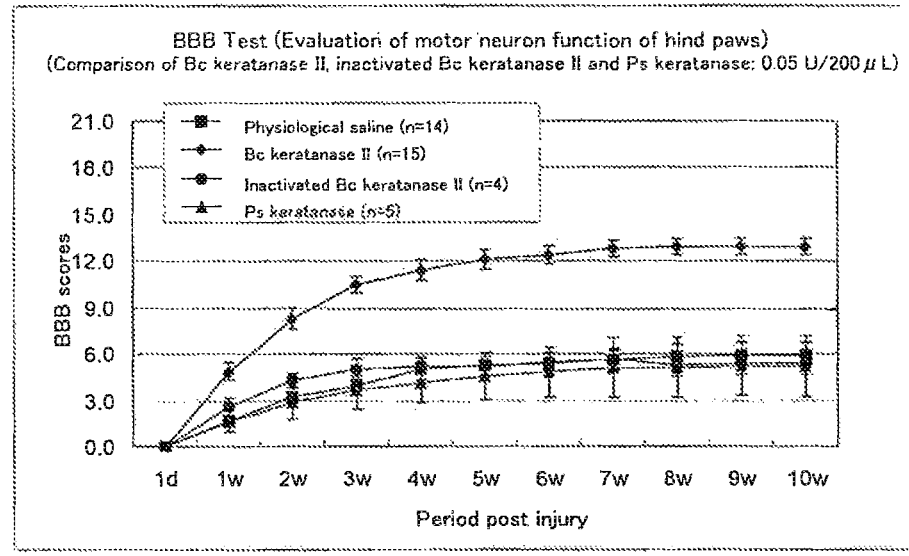
FIG. 5 (the same as above): This is a graph showing the comparison in the therapeutic effects by Bc keratanase II, inactivated Bc keratanase II and Ps keratanase when the administered concentration is 0.05 U/200 μL.

As will be apparent from FIG. 5, when Bc keratanase II, inactivated Bc keratanase II or Ps keratanase was administered in the administered concentration of 0.05 U/200 μL, the effect for the recovery of motor neuron function of hind paws was noted in Bc keratanase II only. From such results, it has now become clear that a substance which is able to be an active ingredient for a recovery treatment of motor neuron function of hind paws among the enzymes which are called keratanase degrading keratan sulfate is keratanase II and that, since inactivated Bc keratanase II is ineffective, the effect of Bc keratanase II is due to its endo-β-N-acetylglucosaminidase activity.

Experimental Result 2: Evaluation of Motor Neuron Function of Hind Paws (Grid Test)

From one week after the injury until 10 weeks thereafter, rats were placed on a net (grid) of 2 cm×2 cm once a week, let them walk for three minutes and then the times of being able to grip the grid by hind paws and total number of steps were measured. In the total number of steps, the rate where the gripping was possible was used as a % grip value and it was expressed by averaging the values of left and right hind paws. The result where each of Bc keratanase II and Ks36 keratanase II was administered in the administered concentration of 0.05 U/200 µL is shown in FIG. 6, and the result where each of them was administered in the administered concentration of 0.000025 U/200 µL is shown in FIG. 7.

Figure 6:
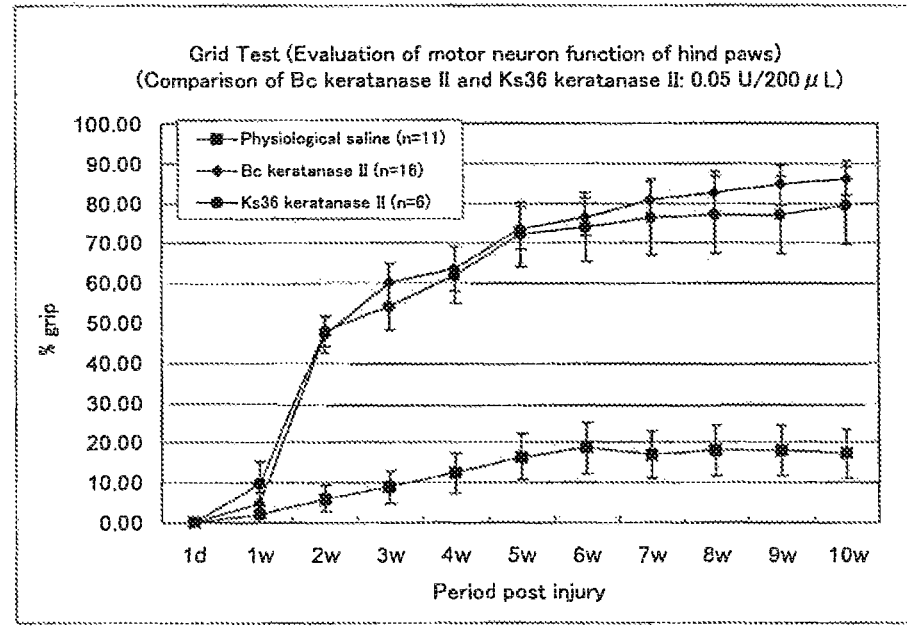
FIG. 6 Experimental Result of Example 1, No. 2: This is a graph showing the comparison in the therapeutic effects by Bc keratanase II and Ks36 keratanase II when the administered concentration is 0.05 U/200 μL in an evaluation of the recovery of hind paw motor function (Grid Test).

As will be apparent from FIG. 6, the % grip values in the groups to which Bc keratanase II and Ks36 keratanase II were administered were nearly the same when the administered concentration was 0.05 U/200 µL and any of them was higher than the % grip value in the group to which physiological saline was administered.

Figure 7:
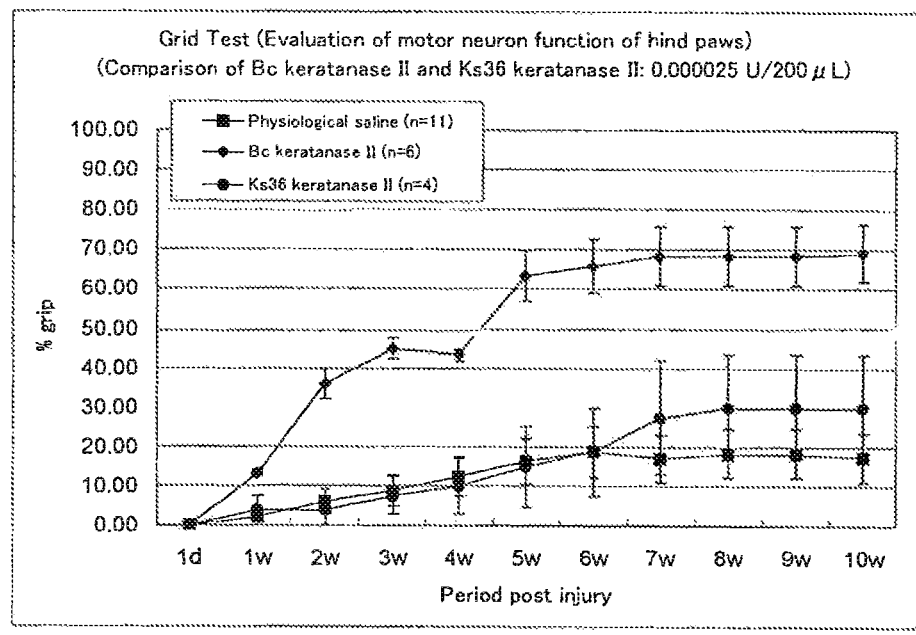
FIG. 7 (the same as above): This is a graph showing the comparison in the therapeutic effects by Bc keratanase II and Ks36 keratanase II when the administered concentration is 0.000025 U/200 μL.

As will be apparent from FIG. 7, when the administered concentration was as low as 0.000025 U/200 µL, the effect for the recovery of motor neuron function of hind paws was noted in Bc keratanase II having an excellent heat stability but it was not noted in Ks36 keratanase II. From such results, it has now become clear that, due to its excellent stability, Bc keratanase II exhibits the efficacy in lower dose and is a better treating agent than Ks36 keratanase II.

Experimental Result 3: Evaluation of Motor Neuron Function of Hind Paws (Foot Print Test)

One day after the injury and once a week from one week after the injury until 10 weeks thereafter, rat hind paws were covered with an ink to record walking patterns during continuous locomotion on a paper of 50 cm. Each of the right and left step of footprints of the hind paws recorded on the paper was measured and their average value was expressed (unit; mm). The result where each of Bc keratanase II and Ks36 keratanase II was administered in the administered concentration of 0.05 U/200 µL is shown in FIG. 8.

Figure 8:
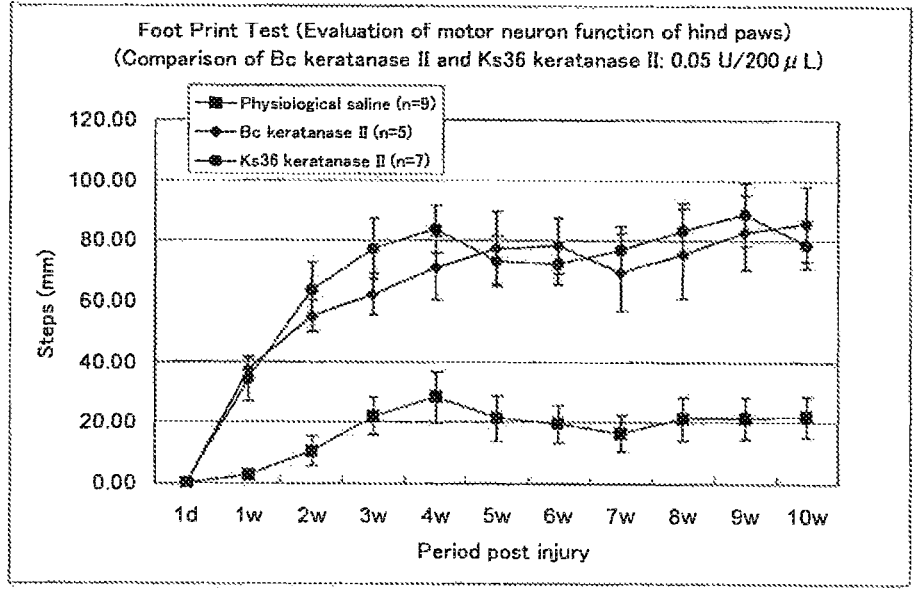
FIG. 8 Experimental Result of Example 1, No. 3: This is a graph showing the comparison in the therapeutic effects by Bc keratanase II and Ks36 keratanase II when the administered concentration is 0.05 U/200 μL in an evaluation of the recovery of hind paw motor function (Foot Print Test).

As will be apparent from FIG. 8, the steps in the groups to which Bc keratanase II and Ks36 keratanase II were administered were longer than the step in the group to which physiological saline was administered whereby, in those administered groups, the recovery of motor neuron function of hind paws was noted.

Experimental Result 4: Evaluation of a Therapeutic/Improving Effect for Thermal Allodynia (Action to Thermal Stimulation of Sensory Neuron: Tail Flick Test)

Before the injury and once a week from one week after the injury until 10 weeks thereafter, tails of rats were dipped in a bath of 55° C. and the time until the rats withdrawn their tails (response time) was measured (unit; second(s)). The measurement of the withdrawal latency time was conducted for three times with intervals of 15 minutes and their average value was expressed. The result where each of Bc keratanase II and Ks36 keratanase II was administered in the administered concentration of 0.05 U/200 µL is shown in FIG. 9.

Figure 9:
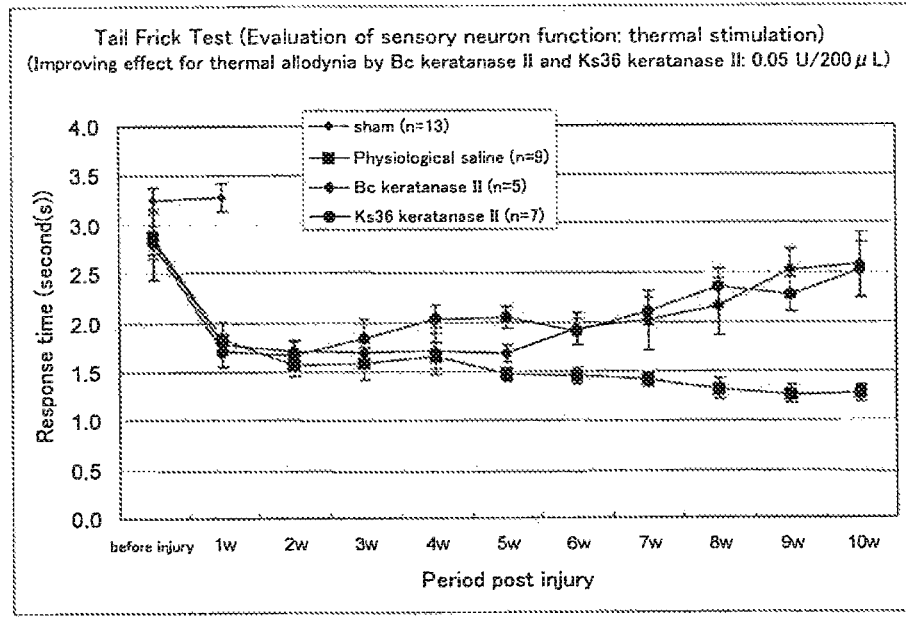
FIG. 9 Experimental Result of Example 1, No. 4: This is a graph showing the comparison in the therapeutic/improving effects by Bc keratanase II and Ks36 keratanase II when the administered concentration is 0.05 U/200 μL in an evaluation of a therapeutic/improving effect for thermal allodynia (Tail Flick Test).

As will be apparent from FIG. 9, in the group to which physiological saline was administered, the response time became short with elapse of time after the injury showing a hypersensitivity reaction to thermal stimulation as compared with before the injury. On the contrary, in the group to which Bc keratanase II and Ks36 keratanase II were administered, although they showed the similar tendency to the case of the group to which physiological saline was administered in an early stage of the injury, the hypersensitivity reaction to thermal stimulation was improved as from the stage of five weeks after the injury and, after eight weeks from the injury, a stable response time almost nearly in the same degree as that before the injury was observed. Thus, in those groups, a significant recovery reaching the normal value of sensory neuron function (therapeutic/improving effect for thermal allodynia) was noted.

Experimental Result 5: Evaluation of a Therapeutic/Improving Effect for Mechanical Allodynia (Action to Pressure Stimulation of Sensory Neuron: Touch Test)

Before the injury and once a week from one week after the injury until 10 weeks thereafter, rats were allowed to stand and habituated for a 15 minutes in a small box. When the rats became calm, von frey filaments (several kinds of filaments where stimulation strengths were different) were applied to the plantar surface of the hind paws from the downside and, with using an up-down method where strong stimulation and weak stimulation were repeated to determine the correct stimulation threshold value (Chaplan, S. R., Bach, F. W., Pogrel, J. W., Chung, J. M., Yaksh, T. L., Quantitative assessment of tactile allodynia in the rat paw., *J. Neurosci. Methods*, 53, 55-63 (1994)), each of right and left pressure stimulations of the filament by which the rat felt the pain and moved the hind paws was measured and expressed in terms of their average value (unit; gram(s)). The result where each of Bc keratanase II and Ks36 keratanase II was administered in the administered concentration of 0.05 U/200 µL is shown in FIG. 10.

Figure 10:
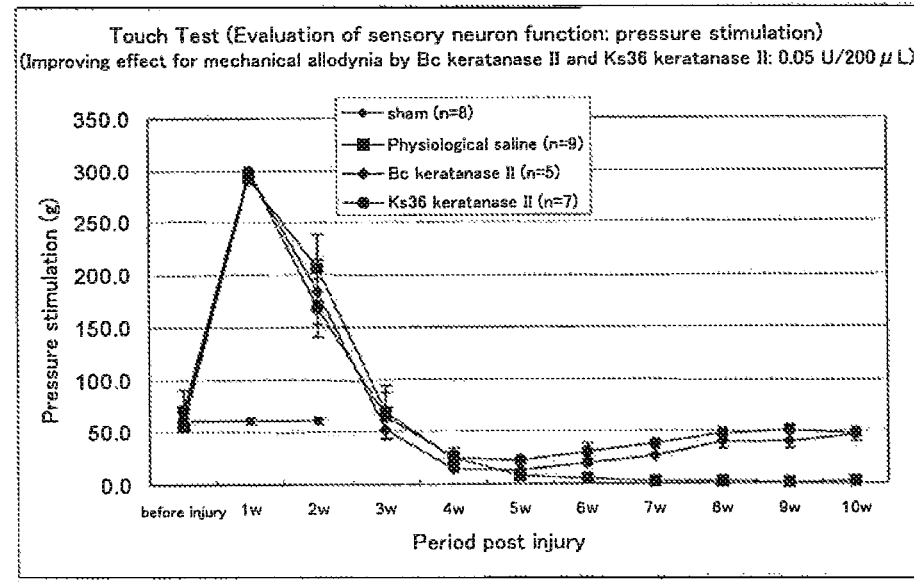
FIG. 10 Experimental Result of Example 1, No. 5: This is a graph showing the comparison in the therapeutic/improving effects by Bc keratanase II and Ks36 keratanase II when the administered concentration is 0.05 U/200 μL in an evaluation of the therapeutic/improving effect for mechanical allodynia (Touch Test).

As will be apparent from FIG. 10, in the group to which physiological saline was administered, the pressure stimulation of the filament showed a high value from one week to two weeks after the injury as compared with the stage before the injury showing an insensitivity reaction to the stimulation to the hind paws. However, as from four weeks after the injury, the pressure stimulation of the filament showed low values as compared with the stage before the injury and, after six weeks from the injury, a sensory hypersensitivity symptom where the response was resulted even by a slight stimulation to the hind paws was noted. On the contrary, in the groups to which Bc keratanase II and Ks36 keratanase II were administered, although they showed the similar tendency to the case of the group to which physiological saline was administered until six weeks after the injury, the sensory hypersensitivity reaction was gradually improved as from seven weeks after the injury. After ten weeks from the injury, the pressure stimulation of the filament nearly in the same degree as that before the injury was observed and, in those groups, a significant recovery reaching the normal value of sensory neuron function (therapeutic/improving effect for mechanical allodynia) was noted.

Example 2

Action for Elongating Neurite Lengths and Action for Suppressing Rho Kinase Activation of Keratanase II Experiment 1: Release of Inhibition of Elongation of Neuronal Axon (Experimental Method)

After primary cortical nerve tissue was collected from the brain of mice of one day from birth (P1), the cortex was finely cut, floated in a calcium and magnesium free Hanks buffer (HBSS) and treated with 0.25% of trypsin and 0.1% of deoxyribonuclease (DNase) at 37° C. for 15 minutes. The isolated neurons were made into a cell suspension of $1\times10^5$ cells/mL by using Neurobasal medium (Basal Medium for Neuronal Cells; Invitrogen) to which 2% of an additive for the neurons incubation (B27 Supplement for Neuronal Cells) was added. After the cell suspension was seeded onto an 8-well chamber applied with a test sample, it was incubated for one night. Twenty-four hours after starting the incubation of the neurons, the chamber slide was fixed with 4% of paraformaldehyde and the neurons were identified by an immunohistochemical means with Neuronal Class IIIβ tubulin (TUJ1) antibody (COVANCE). The neurite lengths were measured of from 80 to 90 neurons per condition, an average value thereof was calculated and shown by a graph. The test sample was the following three types.

(1) that which was applied with 25 μg/mL of poly-L-lysine (Sigma; hereinafter, the same)

(2) that which was applied with 25 μg/mL of poly-L-lysine followed by being applied with an extracellular proteoglycan mixture solution (PG) (0.5 μg/mL, Chemicon; a mixture of Neurocan, Phosphacan, Versican and Aggrecan; hereinafter, the same)

(3) that which was applied with 25 μg/mL of poly-L-lysine followed by being applied with PG (0.5 μg/mL) and Ks36 keratanase II (0.01 U/mL: Seikagaku Corporation).

(Experimental Result)

Figure 11:
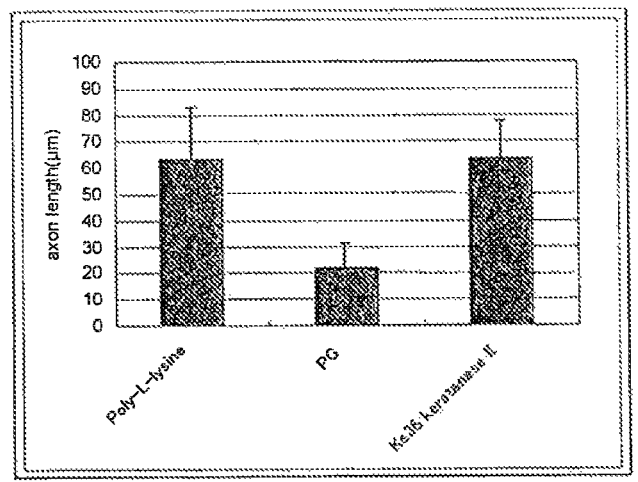
FIG. 11 Experiment of Example 2, No. 1: This is a graph showing a releasing effect of Ks36 keratanase II to a neurite outgrowth-inhibiting action by keratan sulfate.

The result is shown in FIG. 11. As will be apparent from FIG. 11, an elongation of neurite lengths was inhibited about 70% in the presence of PG containing keratan sulfate, while an inhibiting action for elongation of the neurite lengths induced by PG was released to an extent of nearly 100% in the co-presence of Ks36 keratanase II. From the above result, it has now become clear that keratanase II has a releasing effect for an inhibiting action for the elongation of neurite lengths.

Experiment 2: Suppression of Rho Kinase Activation (Experimental Method)

Next, participation of Rho kinase was investigated in order to investigate the action mechanism of keratanase II in the above Experiment 1. The neurons were seeded onto an 8-well chamber to which a test sample was applied by the same manner as in the method of Experiment 1. Twenty-four hours after starting the incubation of the neurons, 15 μM of Y27632 (Rho kinase inhibitor, Sigma) was added to the neurons followed by incubating for 24 hours more. After that, the chamber was fixed with 4% of paraformaldehyde and the neurons were identified by an immunohistochemical means with Neuronal Class IIIβ tubulin (TUJ1) antibody (COVANCE). The neurite lengths were measured of from 80 to 90 neurons per condition, an average value thereof was calculated and shown by a graph. The test sample was the following four types.

(1) that which was applied with 25 μg/mL of poly-L-lysine (Sigma; hereinafter, the same) followed by being applied with 10 μg/mL of laminin (BD Biosciences; hereinafter, the same).

(2) that which was applied with 25 μg/mL of poly-L-lysine followed by being applied with 10 μg/mL of laminin and 20 μg/mL of keratan sulfate (Seikagaku Corporation; hereinafter, the same).

(3) that which was applied with 25 μg/mL of poly-L-lysine followed by being applied with 10 μg/mL of laminin and 40 μg/mL of keratan sulfate.

(4) that which was applied with 25 μg/mL of poly-L-lysine followed by being applied with 10 μg/mL of laminin, 20 μg/mL of keratan sulfate and Ks36 keratanase II (0.01 U/mL, Seikagaku Corporation).

(Experimental Result)

Figure 12:
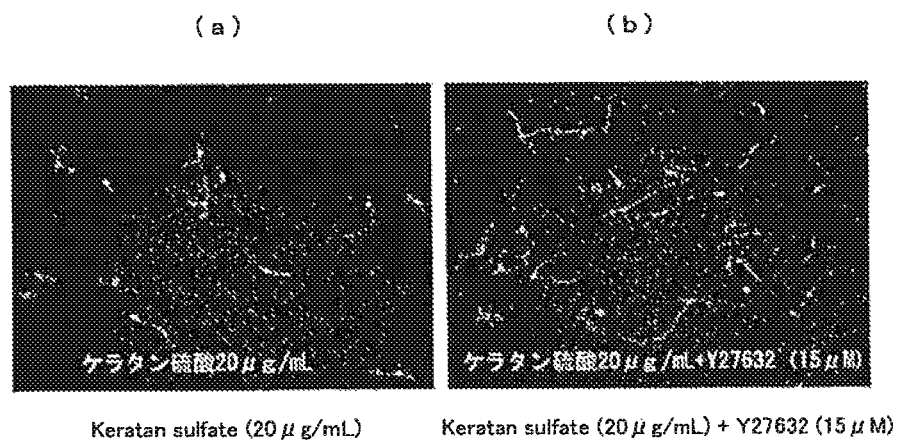
FIG. 12 Experiment of Example 2, No. 2: These are pictures under a fluorescence microscope showing a releasing effect of Y27632 (Rho kinase inhibitor, Sigma) to a neurite outgrowth-inhibiting action by keratan sulfate.
Figure 13:
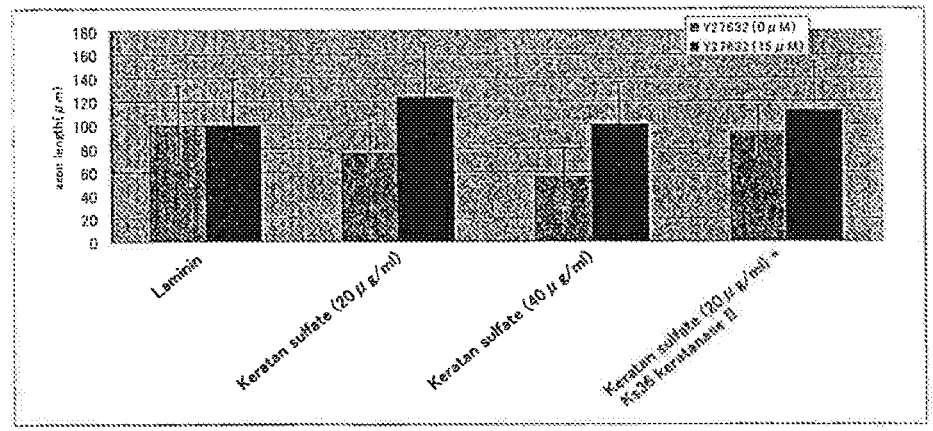
FIG. 13 (the same as above): This is a graph showing an Rho kinase activation suppressing action of Ks36 keratanase II.

FIG. 12 shows the pictures under a fluorescent microscope showing the degree of an elongation of the neurite lengths in (a) the case where Y27632 was not added to the test sample (2) and (b) the case where it was added thereto. FIG. 13 shows the results of measurement of the neurite lengths for each test sample where Y27632 was not added and was added. As will be apparent from FIG. 12 and FIG. 13, an inhibiting action for an elongation of neurite lengths induced by keratan sulfate was released by the addition of Y27632. From such results, it was noted that keratan sulfate induces the inhibition of the elongation of the neurite lengths via an Rho kinase activation. It became also clear that, since the inhibiting action for the elongation of the neurite lengths via an Rho kinase activation by keratan sulfate was released by the co-presence of Ks36 keratanase II even if Y27632 was not added, keratanase II suppresses an Rho kinase activation whereby it achieves a releasing effect for an inhibiting action for elongating neurite lengths by keratan sulfate.

Examples 3

Figure 14:
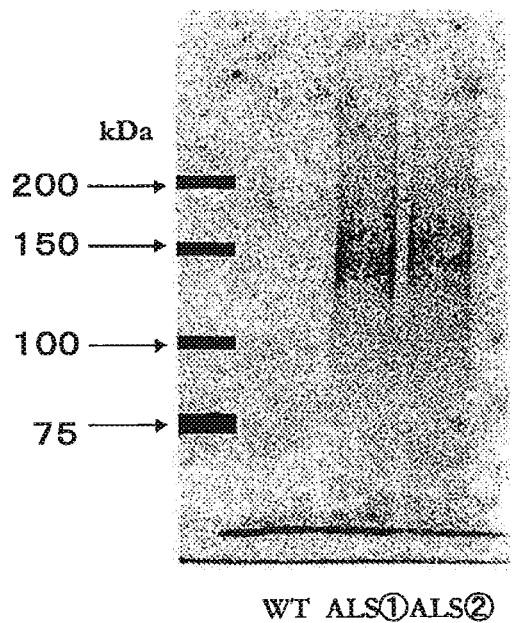
FIG. 14 This is a result of western blotting showing the expression of keratan sulfate in spinal cord of ALS model mice in Example 3.

Expression of Keratan Sulfate in Spinal Cords of Amyotrophic Lateral Sclerosis (ALS) Model Mice SOD1-G93A mice which are ALS model mice were purchased from Jackson Laboratory. Spinal cords were excised from two ALS model mice and, after extraction of protein, Western blotting was carried out. Amount of keratan sulfate was detected by anti-keratan sulfate antibody 5D4 (Seikagaku Corporation). As a result, in ALS model mice, increase of the expression of keratan sulfate was detected as compared with the wild type mice (WT) (FIG. 14).

Figure 15:
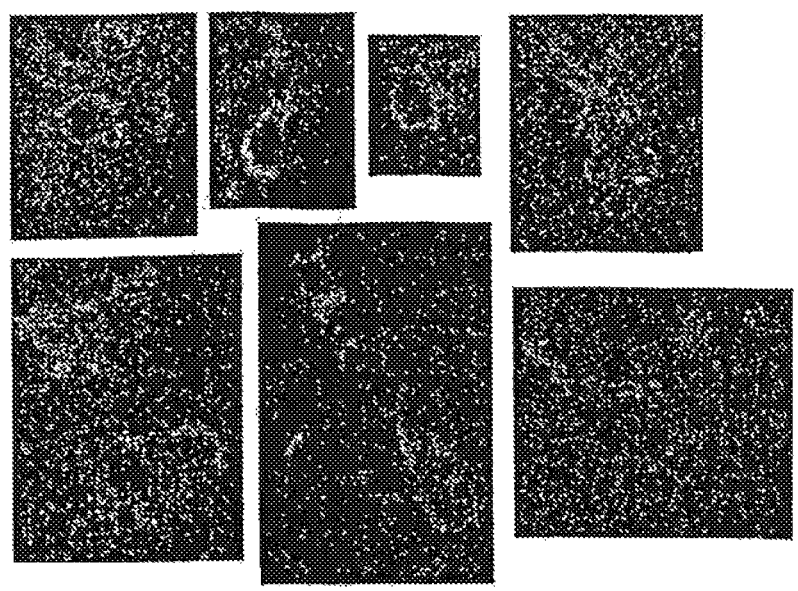
FIG. 15 (the same as above): These are pictures under a fluorescence microscope showing the expression of keratan sulfate in microglia.

Then, the cells expressing keratan sulfate in spinal cord of ALS model mice were investigated by an immunohistochemical means. Spinal cords of ALS model mice were excised and, after tissue sections were prepared, they were subjected to a double staining with anti-keratan sulfate antibody 5D4 and Iba1 which recognizes a specific marker of microglia cells whereupon expression of keratan sulfate in microglia was confirmed (FIG. 15).

ALS has been known that gliosis occurs therein and, from the above result, it was noted that keratan sulfate is not expressed in astrocyte which is a main body of gliosis but is expressed specifically in microglia which has been said to be closely participated in the onset of disease. Such a phenomenon is able to be said to be an expression mode which is specific to ALS when the fact that, in spinal cord injury and brain stab injury, keratan sulfate is expressed not only in microglia but also in oligodendrocyte is taken into consideration.

Preparation Example 1 rBc keratanase II (genetically recombinant type heat resistant keratanase II) was dissolved in physiological saline to prepare a solution preparation where the concentration was 0.000025 U/μL to 0.05 U/200 μL.

INDUSTRIAL APPLICABILITY

The present invention has an industrial applicability in such a respect that an endo-β-N-acetylglucosaminide type enzyme which hydrolyzes an N-acetylglucosaminide bond in a keratan sulfate backbone is able to be provided as an active ingredient for an improving agent for dysfunction of motor neuron and of sensory neuron due to nerve damage such as spinal cord injury or, to be more specific, for an improving agent for neuropathic pain for example.

The invention claimed is:

1. A method for treating neuropathic pain, comprising administering keratanase II as an endo-β-N-acetylglucosaminidase type enzyme which hydrolyzes an N-acetylglucosaminide bond in a keratan sulfate backbone to a patient suffering from neuropathic pain, wherein said keratanase II is administered to a neuropathic site, and wherein said keratanase II is administered at the dose of 0.3 milliunit (mU) to 15000 mU per day to an adult human patient.

2. The method according to claim 1, wherein said keratanase II is a heat-resistant keratanase II having an excellent stability against heat where the optimum reaction temperature is 50 to 60° C.

3. The method according to claim 1, wherein said keratanase II is administered continuously to the neuropathic site.

4. The method according to claim 1, wherein the neuropathic pain is that arising from spinal cord injury.

5. The method according to claim 1, wherein the neuropathic pain is a pain caused by allodynia or hyperalgesic reaction.

* * * * *